(12) United States Patent
Moritz et al.

(10) Patent No.: US 7,691,460 B2
(45) Date of Patent: Apr. 6, 2010

(54) COVERING ELEMENT FOR VEINS, METHOD FOR THE PRODUCTION AND USE THEREOF IN SURGERY

(75) Inventors: Anton Moritz, Frankfurt (DE); Helmut Goldmann, Tuttlingen (DE); Patricia Kreuz, Tuttlingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 903 days.

(21) Appl. No.: 10/485,417

(22) PCT Filed: Jun. 25, 2002

(86) PCT No.: PCT/DE02/02391

§ 371 (c)(1),
(2), (4) Date: Jun. 7, 2004

(87) PCT Pub. No.: WO03/011190

PCT Pub. Date: Feb. 13, 2003

(65) Prior Publication Data

US 2004/0215309 A1     Oct. 28, 2004

(30) Foreign Application Priority Data

Jul. 31, 2001   (DE) ................................ 101 37 414

(51) Int. Cl.
*B32B 1/08*    (2006.01)
*A61F 2/06*    (2006.01)
*A61F 2/50*    (2006.01)

(52) U.S. Cl. .................... 428/36.1; 428/34.1; 428/35.7; 428/36.9; 623/1.1; 623/1.49; 623/1.5; 623/1.51; 623/1.52; 623/1.53

(58) Field of Classification Search ................ 428/34.1, 428/35.7, 35.9, 36.1; 623/1.1, 1.49, 1.5, 623/1.51, 1.52, 1.53

See application file for complete search history.

(56) References Cited

U.S. PATENT DOCUMENTS

| 4,892,539 | A |   | 1/1990 | Koch ............................ 623/1 |
|---|---|---|---|---|
| 5,163,951 | A | * | 11/1992 | Pinchuk et al. ............... 600/36 |
| 5,322,726 | A | * | 6/1994 | Dew .......................... 428/216 |
| 5,628,788 | A | * | 5/1997 | Pinchuk ...................... 623/1.2 |
| 5,645,581 | A |   | 7/1997 | Zurbrügg ........................ 623/1 |
| 5,755,659 | A |   | 5/1998 | Zurbrügg ..................... 600/36 |
| 5,800,514 | A |   | 9/1998 | Nunez et al. |
| 5,904,714 | A |   | 5/1999 | Nunez et al. |
| 6,136,022 | A |   | 10/2000 | Nunez et al. .................. 623/1.1 |
| 6,165,212 | A |   | 12/2000 | Dereume et al. ........... 623/1.13 |
| 6,358,275 | B1 |   | 3/2002 | McIlroy et al. ............. 623/1.28 |
| 2001/0012962 | A1 |   | 8/2001 | Schmitt et al. ............. 623/1.31 |

FOREIGN PATENT DOCUMENTS

DE          43 40 755 C1      6/1995

(Continued)

*Primary Examiner*—Marc A Patterson
(74) *Attorney, Agent, or Firm*—The Nath Law Group; Jerald L. Meyer; Brooks Gifford, III

(57) ABSTRACT

Sheathing for reinforcing natural veins for use as surgical implants in the form of textile netting that is configured by forming a seamless, tubular, essentially pile-less, knit fabric and has loops having large, open apertures having essentially polygonal shapes is made available.

15 Claims, 1 Drawing Sheet

FOREIGN PATENT DOCUMENTS

Figure 1:
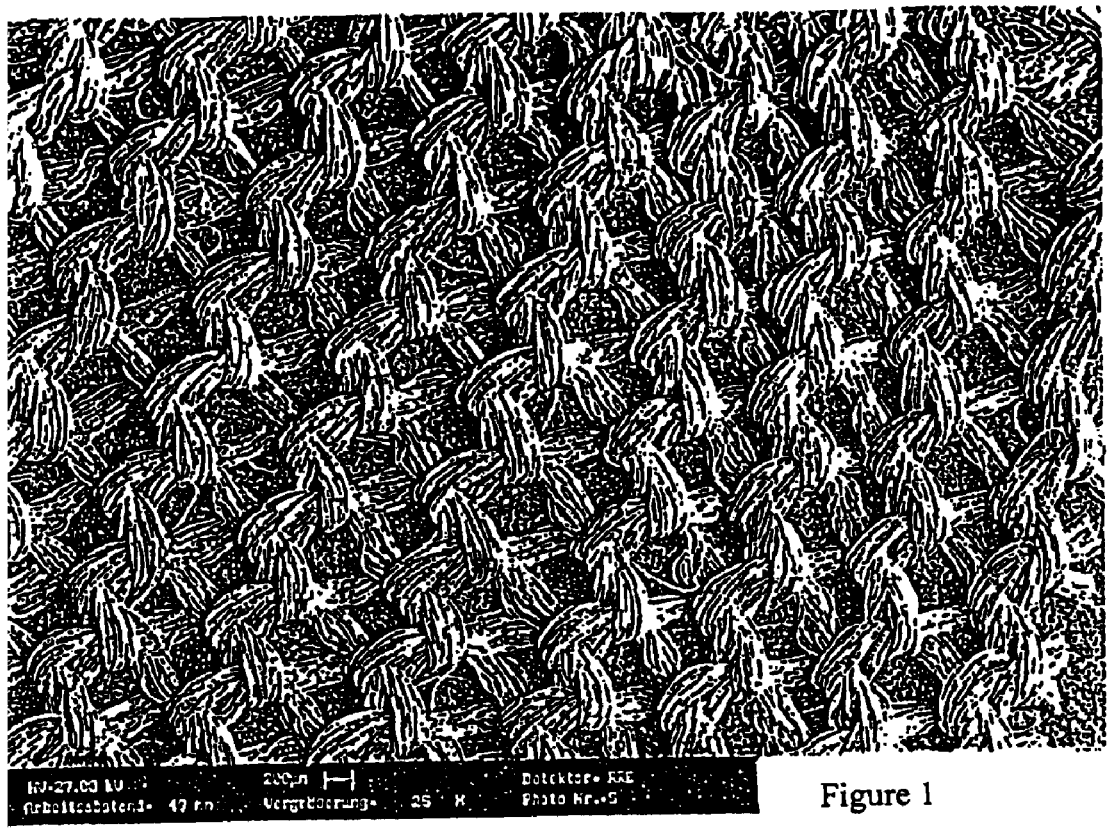

| | | |
|---|---|---|
| DE | 199 10 340 A1 | 9/2000 |
| DE | 199 54 166 | 5/2001 |
| EP | 0 275 653 | 7/1988 |
| EP | 0 687 164 B1 | 12/1995 |
| EP | 0 730 849 B1 | 11/1996 |
| JP | 3280960 | 12/1991 |
| JP | 8509406 | 10/1996 |
| JP | 11511679 | 10/1999 |
| WO | 95/25482 | 9/1995 |
| WO | 99/40875 | 8/1999 |
| WO | WO 99/11198 | 11/1999 |
| WO | 00/54703 | 8/2000 |
| WO | 01/89594 A2 | 11/2001 |
| WO | WO 01/89594 A2 | 11/2001 |

\* cited by examiner

COVERING ELEMENT FOR VEINS, METHOD FOR THE PRODUCTION AND USE THEREOF IN SURGERY

BACKGROUND OF THE INVENTION

1. Field of the Invention

The present invention concerns a sheathing for veins, a method for its manufacture, and its application in surgery.

2. Description of the Related Art

Medicine is frequently confronted with the task of treating cardiovascular diseases, such as arteriosclerosis for instance, caused by changes in blood vessels. Modern surgery employs, in addition to, e.g., deobliteration methods, substitute-vessel implants in the form of bypasses for reconstructing arterial vessels. Known, for example, are vessel implants manufactured from synthetic materials, or synthetic materials combined with natural materials.

Detrimental interactions with the physiological environment in patients' bodies may occur if full-synthetic materials are employed. Serious complications, such as thrombosis or restenosis of vessel implants, that may require expensive post operations may occur when synthetic materials are substituted for coronary or peripheral vessels with small lumen. It is thus desirable to employ implants formed from natural vessel material, since they beneficially affect natural endothelialization and the anti thrombogenic properties of vessel walls. Such biological substitute-vessel materials are generally obtained from veins. However, implanting veins in the arterial vessel system may cause increases in wall thickness to occur during arterialization. If those increases are accompanied by intimahyperplasy due to the differing compliances of veins and arteries, they may ultimately lead to restenosis of the implants. It will be beneficial to externally encase or reinforce native veins in order that they will be reliably able to perform their intended function as, for example, a coronary or peripheral bypass for arterial blood transport, over the long term. External sheathing or stiffening ribs can adapt the compliance of natural vein material to suit the arterial system and thus both reduce incidences of intimahyperplasy and allow achieving high non closure rates over the long term. Moreover, the aforementioned sheathing will also allow implantation of varicose, ectatic, or thin-walled veins that have not been employed to date due to their unfavorable hemodynamic properties. The latter will be the only means for employing vessel materials from patients' own bodies as substitutes for vessels having small lumen, particularly in the case of patients suffering from multiple vessel imperfections.

A vessel prosthesis where a woven sheathing is drawn over a natural blood vessel is known from German Patent DE 4340755. A natural blood vessel spirally wrapped in crossed fibers is described in European Patent EP 687164. U.S. Pat. No. 5,645,581 discloses a tube, whose manufacture is described in U.S. Pat. No. 5,755,659, having crossed fibers spirally wrapped around its longitudinal axis.

According to German Patent DE 19910340, a tube, sheath, or tubing is employed as sheathing for a vein to be used as artery prosthesis. An external reinforcement for vessel prostheses having a duo layer, tubular, polymer-fiber sheathing is known from World Patent WO 00/54703.

The known reinforcements for vessel material have a number of disadvantages. For example, numerous, complex, procedures are required for preparing them and attaching them to implant vessels. Additional tissue adhesives are required in order to attach the reinforcements. Reinforcements based on metals may adversely impact handling of prostheses and foster incompatibility reactions. Problems, particularly problems in the anastomosis area, may occur due to loose ends of wires.

The problem addressed by the invention is thus making available a sheathing for veins that will overcome the problems arising from the state of the art, will reinforce veins to be employed as surgical implants for use as durable vessel substitutes, may be simply and inexpensively manufactured following ordinary manufacturing procedures and manufactured on ordinary manufacturing equipment, and will be simply and reliably applicable in surgery.

SUMMARY OF THE INVENTION

That problem is solved by a sheathing for reinforcing natural veins for use as surgical implants in the form of textile netting that is fabricated by forming a seamless, tubular, essentially pile-less, knit fabric and has loops having large, open apertures having essentially polygonal shapes, in particular, polygonal shapes having rounded corners.

The invention also comprises a method for manufacturing a sheathing for reinforcing natural veins for use as a surgical implant in the form of textile netting fabricated by forming a seamless, tubular, essentially pile-less, knit fabric that has loops having large, open apertures having essentially polygonal shapes.

The present invention is particularly suited to use as sheathing for reinforcing native veins in order to provide surgical implants for use as vessel substitutes in human medicine and veterinary medicine.

The vein sheathing may beneficially be manufactured in the form of open-pored, textile tubing by means of knitting. In the case of one embodiment, the tubing may be manufactured on ordinary circular knitting machines used for manufacturing small-bore tubing. In the case of another embodiment, a dual-bar raschel machine may be used for manufacturing the tubing. Knitting equipment is generally known to specialists in the field, and thus shall not be explained in detail here.

In the case of one embodiment, vein sheathing according to the invention may be formed by circular knitting employing plain-tricot interlocking. In the case of another, preferred, embodiment, vein sheathing according to the invention may be formed by knitting employing a combination of interlocking techniques. Tricot-Atlas, tricot-strand, strand/weft, and combinations employing fillet needles may be mentioned as examples of such combined knitting techniques. According to the invention, knit fabric knit employing tricot-Atlas interlocking is preferred for sheathing veins. However, various other types of knit fabrics and combination knits, such as open meshes or closed meshes, may be employed.

The netting's polygonal loops may have various shapes, depending upon the knitting technique chosen. In the case of one embodiment, the netting's loops may be rhombic. Rhombic loops may be formed, particularly in the case of plain-tricot fabrics. In particular, the clear diameter of the rhombs may fall within the range 100 μm to 600 μm, in particular, within the range 100 μm to 400 μm, or, if larger loops are desired, preferably within the range 300 μm to 600 μm. In the case of knit fabrics knit employing tricot-Atlas interlocking, loops having, in particular, honeycomb shapes, may be formed by rounding off corners. The clear diameter of the loops may, preferably, fall within the range 400 μm to 1,600 μm, in particular, within the range 800 μm to 1,200 μm, or, particularly preferred, within the range 600 μm to 1,000 μm.

It will be particularly beneficial if the tubular knit fabric is essentially formed from biocompatible polymer fibers. Examples of such biocompatible polymers are synthetic polymers in the form of homopolymers, copolymers, terpolymers or polymer blends, natural polymers, or combinations of synthetic and natural polymers. Employment of resorbable, synthetic polymers is also feasible. In the case of a preferred embodiment of the vein sheathing according to the invention, a high-capillarity polyester yarn fabricated from polyethylene terephthalate (PET) is employed. PET is noted for its good biocompatibility, and is thus particular suited for use as an implant material.

According to the invention, the sheathing for veins exhibits essentially no pile. The knit fabric may thus have essentially smooth surfaces on its outer and inner walls. In the case of a special embodiment, the sheathing may be essentially free of textured fibers.

The vein sheathing may be beneficially formed from multifilament yarn. The sheathing according to the invention may be formed from yarn having 2 to 500 filaments, in particular, having 5 to 250 filaments, and preferably having 10 to 100 filaments. The yarn employed according to the invention may have a gauge of, preferably, 50f40 dtex. The knit fabric of the sheathing according to the invention may have a mesh width falling within the range 100 μm to 1,000 μm, in particular, 300 μm to 600 μm.

In the case of plain-tricot interlocking, which is also termed "single-tricot interlocking," knitting employs a single guide bar only. A suitable choice of the number of strands in the yarn and the course density and wale density of the knit fabric will allow adjusting the inner diameter of the knit tubing for sheathing veins as desired. In the case of tubular sheathing knit employing single interlocking, in particular, plain-tricot interlocking, the number of strands may beneficially fall within the range 5 to 25, the course density may beneficially fall within the range 10 to 20 per centimeter, the wale density may beneficially fall within the range 15 to 25 per centimeter, and the nominal diameter may beneficially fall within the range 2 mm to 10 mm. Knit fabric having low wall thicknesses will be the result, particularly in the case of plain-tricot interlocking. The wall thicknesses of plain-knit tubing and plain-tricot tubing, may preferably fall within the range 0.10 mm to 0.25 mm.

In the case of the combined knitting technique, in particular, knitting employing tricot-Atlas interlocking, knitting employs a pair of guide bars and special needles. In particular, the knit tubing obtained has a structure similar to that of a honeycomb. Yarn having fewer strands may be employed in order to obtain a mesh having a looser structure. The inner diameter of the knit tubing for encasing veins may be adjusted as desired by suitably choosing the number of strands in the yarn employed and the course density and wale density of the knit fabric. In the case of tubular sheathing knit employing combined interlocking techniques, in particular, tricot-Atlas interlocking, the number of strands may beneficially fall within the range 15 to 90, the course density may beneficially fall within the range 20 to 40 per centimeter, the wale density may beneficially fall within the range 20 to 30 per centimeter, and the nominal diameter may beneficially fall within the range 2 mm to 15 mm. Wall thicknesses may preferably fall within the range 0.10 mm to 0.30 mm, in particular, may fall within the range 0.15 mm to 0.25 mm. According to the invention, a yarn having a gauge of 50f40 dtex may be preferably employed.

Due to the tighter interlooping of the strands of yarn in the case of the combined knitting technique, the combined knitting technique yields more stable wales and courses than in the case of plain-tricot interlocking. Such a knit fabric may exhibit lower stretchability and greater resistance to distortion. Knit tubing having lower lumen expandability may be obtained in this manner. Knit fabrics according to the invention thus have better abilities to resist stresses due to arterial blood pressure.

Structural features of knit fabrics for vein sheathings manufactured employing plain-tricot interlocking and tricot-Atlas interlocking according to those knitting techniques described as preferred embodiments will be more clearly evident from the accompanying figures.

FIG. 1 depicts a 25×-magnification of a plain-tricot knit fabric. The loop apertures formed in the knit fabric have approximately rhombic to square shapes having clear widths falling within the range 300 μm to 600 μm. The strands of yarn are singly interlooped along the courses and wales, which allows a certain amount of distortion of the loops and stretching of the knit fabric.

Figure 2:
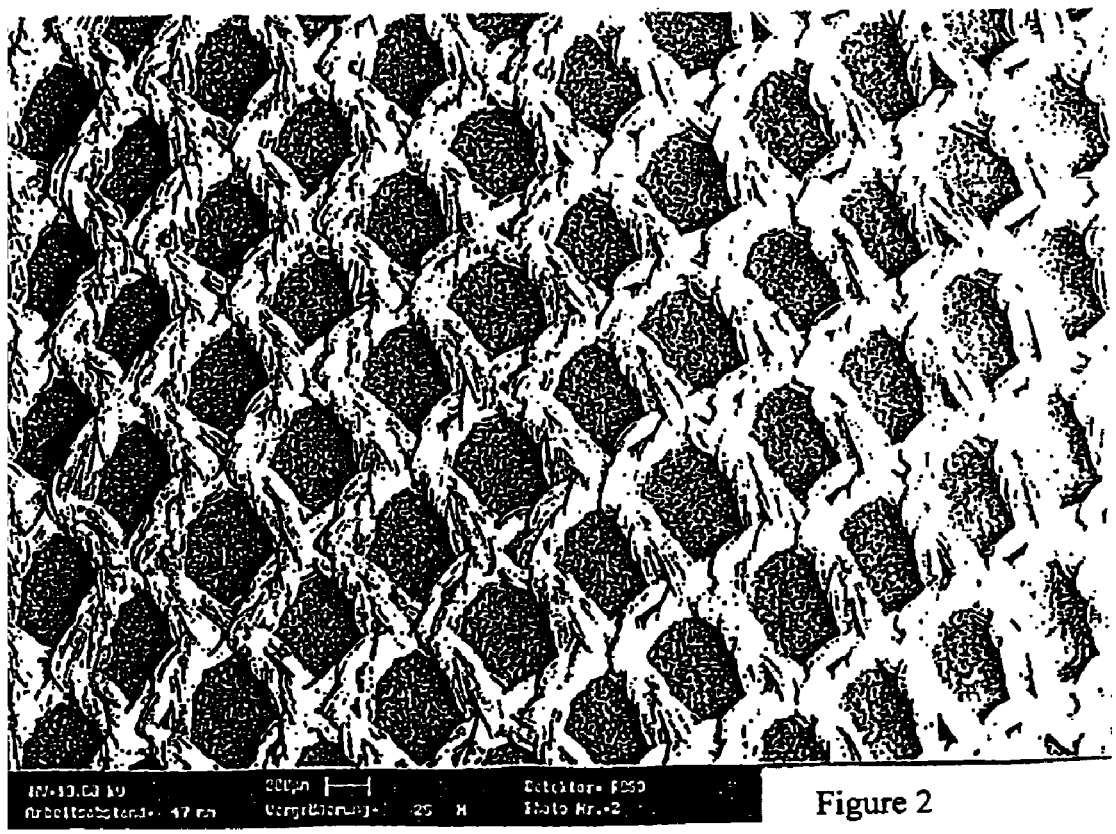

FIG. 2 depicts a 25×-magnification of a tricot-Atlas knit fabric. The loop apertures formed in the knit fabric have approximately honeycomb to rectangular shapes having clear widths falling within the range 400 μm to 1,200 μm, in particular, falling within the range 600 μm to 800 μm. The strands of yarn are also interlooped along the courses and wales in order to yield greater resistance to distortion of the loops.

Knit tubing obtained employing the knitting techniques described above may be pretreated in manners that will make it suitable for sheathing veins. In the case of one embodiment of the invention, the untreated knit fabric may be pretreated by cleansing. In the case of another embodiment of the invention, the untreated knit fabric may be pretreated by thermal shrinking and cleansing.

Cleansing of the untreated knit fabric may be performed in three stages. The material is initially placed in hot water at a temperature of 60° C. and stirred. Residual moisture is then extracted in an extraction apparatus using isopropanol, which will also remove any avivage residues. Finally, the knit fabric is pretreated once again, this time in hot water at a temperature of 40° C. Following cleansing, the knit tubing is dried in a suitable manner, for example, in a laminar-flow box.

In the case of another embodiment, the untreated knit tubing may also be pretreated by shrinking, in which case, shrinking will be performed prior to the cleansing described above. Shrinking may be performed by dipping the knit tubing in boiling water and allowing to remain therein for a suitable period.

Cleansed and, if shrinking has been performed, shrunk, knit tubing may be drawn onto a metal mandrel, each end of the tubing clamped to the respective end of the mandrel, and thermoset at 160° C., which will cause the inner diameter of the knit tubing to expand to varying extents relative to the declared inner diameter of the untreated material, a phenomenon that will be described in detail under Examples 4 and 5, below. Thermosetting may be performed in a single stage. Thermosetting may be alternatively performed in two stages, in which case, the knit tubing will be expanded to an even greater extent.

Knit tubing is preferably thermoset without regard to any pretreatment by shrinking it may have received. In other words, the thermosetting process employed is not determined by the type of pretreatment by shrinking that may have been employed. Since the ends of the knit tubing are clamped to the respective ends of the metal mandrel during thermosetting, it will no longer be able to shrink by much following thermosetting, which, in the case of non preshrunk knit tubing, will lead to larger pores than in the case of shrunk knit tubing. Sheathing according to the invention may beneficially be characterized by the fact that it retains its shape.

The retaining clamps may be removed and the vein sheathing cut to lengths ranging from about 10 cm to 60 cm, preferably ranging from about 10 cm to 30 cm, and packed once thermosetting has been concluded and the metal mandrel has cooled down to room temperature.

Determinations of the normalized radial tensile strengths of various samples knit employing plain-tricot interlocking and combined knitting techniques, such as tricot-Atlas interlocking, showed that the tensile strengths of the knit tubing fell within the range 2 N/mm to 10 N/mm, in particular, fell within the range 2 N/mm to 6 N/mm, depending upon the type of knitting involved and the treatment that the knit tubing had received. The radial tensile strength of knit tubing that had not been preshrunk was less than that of knit tubing that had been preshrunk.

Measurements of the longitudinal tensile strengths of plain-tricot knit tubing yielded values ranging from 70 N to 100 N for samples that had been preshrunk and had not been preshrunk.

The tensile elasticities of the vein sheathing along the radial direction were determined for forces ranging from 2 N to 12 N. Elastic elongations in the radial direction ranging from 3% to 10%, in particular, ranging from 5% to 8%, for plastic elongations of the same order of magnitude ranging from 5% to 15%, in particular, ranging from 6% to 13%, were determined for samples knit employing plain-tricot interlocking and combined interlocking techniques.

The sheathing for veins according to the invention may be cut to suitable lengths and suitably packed, ready for use, in order to make it available for use in surgery. In particular, the sheathing material according to the invention may be sterilized in a suitable manner. A suitable sterilization method may be either chosen from the usual physical or chemical methods for deactivating microorganisms or be a combination of such methods. One possible sterilization method includes treatment with ethylene oxide. Sterilization of sheathing according to the invention may preferably be performed employing γ-radiation.

The vein material to receive sheathing according to the invention involved is a natural vein taken from a mammal. Such veins, or segments of veins, may be taken from deceased donors. Alternatively, such veins, or segments of veins, may be taken from living donors. Vein donors may be animals, for example, pigs. Vein donors may be human beings. It will be particularly preferable if the vein to be sheathed may be taken from the patient who is to receive the sheathed vessel implant. Such an embodiment is particularly preferable, since healing of the patient's bodily tissues without any problems arising is to be expected and incompatibility reactions to the implant may be minimized. No additional attachment of the sheathing using tissue adhesives will be necessary if a natural vein is sheathed according to the invention, which will allow further reducing the technical effort involved in implantation and risks of complications occurring.

In the following, the present invention will be explained through detailed descriptions of particular embodiments in the form of examples. In the examples, the individual features of the invention may be implemented either alone, or in combination with other features thereof. The examples are for the purpose of explaining the invention and making it more readily comprehensible only, and shall not be construed as representing restrictions of any kind.

DETAILED DESCRIPTION OF PREFERRED EMBODIMENTS

Example 1

Manufacture of Knit Tubing

A knit fabric knit employing tricot-Atlas interlocking employing a pair of guide rails is manufactured as the raw material for the vein sheathing. Polyethylene-terephthalate-fiber yarn in a gauge of 50f40 dtex is knit at a course density of about 35 per centimeter and a wale density of about 25 per centimeter. Yarn having 20 strands will yield knit tubing having a nominal diameter of 4 mm. Yarn having 80 strands will yield knit tubing having a nominal diameter of 14 mm.

Example 2

Pretreatment by Cleansing

The untreated knit tubing obtained under Example 1 is cleansed, without shrinking it, by stirring it in hot, demineralized water at a temperature of 60° for 30 min. Under a second step, the material is cleansed and any residues present extracted using isopropanol in a Soxhlet apparatus for a period ranging from 15 min to 3 h, depending upon the quantity of material involved, which will eliminate any avivage residues. In a third cleansing step, the material is, once again, incubated in hot water, this time at a temperature of 40° C., for 10 min, under constant stirring. In a final step, the cleansed material is dried overnight in a laminar-flow box.

Example 3

Pretreatment by Shrinking

The untreated knit tubing obtained under Example 1 is shrunk in boiling, demineralized water at a temperature falling within the range 97° C. to 100° C. for 5 min. In an initial step, the shrunk material is then cleansed in hot, demineralized water at a temperature of 60° C., under constant stirring. In a second step, the material is cleansed and any residues present extracted using isopropanol in a Soxhlet apparatus for a period ranging from 15 min to 3 h, depending upon the quantity of material involved, which will eliminate any avivage residues. In a third cleansing step, the material is, once again, incubated in hot water, this time at a temperature of 40° C., for 10 min, under constant stirring. In a final step, the shrunk, cleansed material is dried overnight in a laminar-flow box.

Example 4

Thermosetting Plain-Tricot Knit Fabrics

Knit tubing pretreated according to Example 3 having a declared inner diameter of 3 mm is cut to a length of 40 cm, drawn onto a metal mandrel having an outer diameter of 6 mm, and thermoset in a single step. Knit tubing having declared inner diameters of 4 mm or 5 mm may be drawn onto mandrels having outer diameters of 7 mm or 8 mm, respectively, and thermoset, where the final inner diameter of the vein sheathing will equal the outer diameter of the metal mandrel employed.

In the case of a two-step thermosetting, tubing having a declared inner diameter of 3 mm is drawn onto a metal mandrel having an outer diameter of 5 mm in an initial step of the thermosetting procedure and drawn onto a mandrel having an outer diameter of 6 mm in a second step of the thermosetting procedure, and thermoset following each step. Tubing having a declared inner diameter of 4 mm is expanded to yield inner diameters of 7 mm and 8 mm and thermoset following these same procedures.

Example 5

Thermosetting Tricot-Atlas Knit Fabrics

Unlike the plain-tricot knit tubing described under Example 4, tricot-Atlas knit tubing may be only slight expanded. In the case of single-step thermosetting, such tricot-Atlas tubing having a declared inner diameter of 7 mm is drawn onto metal mandrels having outer diameters of 6 mm, 7 mm, or 8 mm and thermoset. Cleansed, shrunk knit tubing may be treated in the same manner. In the case of two-step thermosetting, tricot-Atlas tubing having a declared inner diameter of 7 mm is initially thermoset on a metal mandrel having an outer diameter of 7 mm and thermoset a second time on another metal mandrel having an outer diameter of 8 mm once it has cooled.

Example 6

Properties of Vein Sheathing

Vein sheathing manufactured according to the examples described above will have well-defined geometric and physical properties.

The mean wall thickness of sheathing manufactured employing plain-tricot interlocking is 0.17 mm±0.01 mm. The mean wall thickness of sheathing manufactured employing tricot-Atlas interlocking falls within the range 0.22 mm±0.01 mm to 0.23 mm±0.01 mm.

Measurements of their radial tensile strengths indicate a strong dependence of the values obtained therefore on the type of pretreatment employed. Shrinking in boiling water may significantly increase their tensile strengths in some cases.

The tensile strengths determined for typical samples appear listed in Table 1, below:

TABLE 1

| Type of Knit Tubing | Manufacturing Parameters/ Method | Normalized Radial Tensile Strength [N/mm] and the Number of Strands in the Yarn Employed (n) |
|---|---|---|
| Plain tricot | Inner diameter expanded from 4 mm to 8 mm (in two steps, 4 mm → 7 mm, and 7 mm → 8 mm), following preshrinking in boiling water. | 4.5 ± 1.6 n = 13 |
| | Inner diameter expanded from 3 mm to 6 mm (in two steps, 3 mm → 5 mm, and 5 mm → 6 mm), following preshrinking in boiling water. | 4.6 ± 1.6 n = 26 |
| | Inner diameter expanded from 5 mm to 8 mm (in a single step), not preshrunk. | 2.3 ± 0.6 n = 13 |
| | Inner diameter expanded from 3 mm to 6 mm (in two steps, 3 mm → 5 mm, and 5 mm → 6 mm), not preshrunk. | 3.5 ± 1.0 n = 13 |
| Tricot-Atlas N | Inner diameter held constant at 6 mm (thermoset in a single step), following preshrinking in boiling water. | 4.9 ± 0.4 n = 13 |
| | Inner diameter held constant at 6 mm (thermoset in a single step), not preshrunk. | 4.4 ± 0.4 n = 13 |
| Tricot-Atlas N2 | Inner diameter held constant at 6 mm (thermoset in a single step), following preshrinking in boiling water. | 5.9 ± 0.4 n = 13 |
| | Inner diameter held constant at 6 mm (thermoset in a single step), not preshrunk. | 4.6 ± 0.4 n = 13 |

Example 7

Compliances of Sheathed Veins

In order to test the compliances of veins having sheathing, sheep jugular veins were sheathed in various types of tubular polyester (Dacron) netting at a flow rate of 300 ml/min and a modulating pressure having an amplitude of 50 mm(Hg) and tested for their dynamic compliances and diameters at various pressures. The measured values were compared to those for native sheep carotid arteries and jugular veins and a vein substitute fabricated from polytetrafluoroethylene (PTFE).

The diameter of the sheep jugular veins employed was 14.7 mm±2.92 mm, and their circumferential compliance was 2.78±1.4%/100 mm(Hg). The diameter of the sheep carotid arteries employed was 6.6 mm±0.27 mm, and their circumferential compliance was 3.3±0.9%/100 mm(Hg). The circumferential compliance of the PTFE vein substitute employed was 0.6±0.05%/100 mm(Hg). The outer diameters of the stents decreased to mean values of 7.4 mm±0.12 mm, and thus virtually equals the artery diameter. The circumferential compliances of veins equipped with stents varied from 1.98%/100 mm(Hg) to 0.74%/mm(Hg), depending upon the structures of the stents involved.

Veins sheathed in a textile construction, as stipulated by the invention, exhibited a nonlinear compliance, as is observed in the case of natural blood vessels, particularly in the case of arteries. Long-term efficacies and extended service lives of the sheathed, native, vessel prostheses may thus be expected, where incidences of intimahyperplasy will also be reduced.

What is claimed is:

1. A surgical implant comprising vein sheathing in the form of textile netting for reinforcing natural veins having a seamless, tubular, essentially pile-less, warp knit fabric and having loops having large, open apertures having essentially polygonal shapes, and having a course density falling within the range 10 to 40 per centimeter and a wale density falling within the range 15 to 30 per centimeter, wherein the knit fabric employs tricot-Atlas interlocking.

2. The surgical implant according to claim 1, wherein it is essentially formed from biocompatible polymer fibers.

3. The surgical implant according to claim 1, wherein it is formed such that it is essentially free of textured fibers.

4. The surgical implant according to claim 1, wherein it is formed from multifilament yarn.

5. The surgical implant according to claim 1, wherein it is formed from yarn having 2 to 500 filaments.

6. The surgical implant according to claim 1, wherein it is formed from yarn having a gauge of 50f40 dtex.

7. The surgical implant according to claim 1, wherein it has a mesh spacing falling within the range 100 μm to 1,000 μm.

8. The surgical implant according to claim 1, wherein the inner boundaries of the netting's loops are rounded.

9. The surgical implant according to claim 1, wherein it is formed such wherein it has a wall thickness falling within the range 0.05 mm to 0.5 mm.

10. The surgical implant according to claim 1, wherein it is formed such that it has a nominal diameter falling within the range 2 mm to 15 mm.

11. The surgical implant according to claim 1, wherein it is pretreated by thermal shrinking.

12. The surgical implant according to claim 1, wherein it is thermoset.

13. The surgical implant according to claim 1, wherein it is largely dimensionally stable.

14. A method for manufacturing a surgical implant comprising a vein sheathing in the form of textile netting for reinforcing natural veins wherein it is configured by forming a seamless, tubular essentially pile-less, warp knit fabric having loops having large, open apertures having essentially polygonal shapes, and having a course density falling within the range 10 to 40 per centimeter and a wale density falling within the range 15 to 30 per centimeter, wherein the knit fabric employs tricot-Atlas interlocking.

15. The method according to claim 14, wherein the vein sheathing is configured by knitting a multifilament yarn.

* * * * *